US011462323B2

(12) United States Patent
Koblenski et al.

(10) Patent No.: US 11,462,323 B2
(45) Date of Patent: Oct. 4, 2022

(54) DECREASED LATENCY WIRELESS COMMUNICATION FOR USE WITH MEDICAMENT DEVICES

(71) Applicant: Reciprocal Labs Corporation, Madison, WI (US)

(72) Inventors: Samuel A. Koblenski, Madison, WI (US); Benjamin J. Kopp, Verona, WI (US); Justin Conrad Krosschell, Sioux Falls, SD (US); John David Van Sickle, Oregon, WI (US); Gregory F. Tracy, Madison, WI (US)

(73) Assignee: Reciprocal Labs Corporation, Madison, WI (US)

( * ) Notice: Subject to any disclaimer, the term of this patent is extended or adjusted under 35 U.S.C. 154(b) by 0 days.

(21) Appl. No.: 17/043,586

(22) PCT Filed: Mar. 28, 2019

(86) PCT No.: PCT/US2019/024552
§ 371 (c)(1),
(2) Date: Sep. 29, 2020

(87) PCT Pub. No.: WO2019/191408
PCT Pub. Date: Oct. 3, 2019

(65) Prior Publication Data
US 2021/0020309 A1    Jan. 21, 2021

Related U.S. Application Data

(63) Continuation of application No. 15/940,950, filed on Mar. 29, 2018, now Pat. No. 10,388,412.

(51) Int. Cl.
*G16H 40/67* (2018.01)
*H04W 76/14* (2018.01)
(Continued)

(52) U.S. Cl.
CPC ............... *G16H 40/67* (2018.01); *G06F 8/65* (2013.01); *G16H 20/13* (2018.01); *G16H 40/40* (2018.01);
(Continued)

(58) Field of Classification Search
CPC ...................................................... H04W 4/80
See application file for complete search history.

(56) References Cited

U.S. PATENT DOCUMENTS 8,807,131 B1 * 8/2014 Tunnell ............... A61M 16/021
128/200.23
9,550,031 B2   1/2017 Van Sickle et al.
(Continued)

FOREIGN PATENT DOCUMENTS

JP    2013-545167 A   12/2013
JP    2017-531465 A   10/2017
(Continued)

OTHER PUBLICATIONS

PCT International Search Report and Written Opinion for PCT/US2019/024552, dated Jun. 6, 2019, 17 Pages.
(Continued)

*Primary Examiner* — Wen W Huang
(74) *Attorney, Agent, or Firm* — Fenwick & West LLP

(57) ABSTRACT

This present disclosure describes a computer-implemented method for updating a plurality of parameters on a medical inhaler sensor via a wireless connection by a client device. The client device stores the plurality of parameters for the medical inhaler sensor on the client device. The client device updates one or more parameters of the plurality of parameters on the client device. The client device receives a plurality of periodic chirps from the medical inhaler sensor, and can establish the wireless connection with the medical inhaler sensor in in response to having received a chirp.
(Continued)

Through the wireless connection, the client device transmits the updated one or more parameters of the plurality of parameters to the medical inhaler sensor.

17 Claims, 8 Drawing Sheets

(51) Int. Cl.
*H04W 4/80* (2018.01)
*G06F 8/65* (2018.01)
*H04L 43/10* (2022.01)
*H04L 67/00* (2022.01)
*G16H 40/63* (2018.01)
*G16H 40/40* (2018.01)
*G16H 20/13* (2018.01)

(52) U.S. Cl.
CPC .............. *G16H 40/63* (2018.01); *H04L 43/10* (2013.01); *H04L 67/34* (2013.01); *H04W 4/80* (2018.02); *H04W 76/14* (2018.02)

(56) References Cited

U.S. PATENT DOCUMENTS

| | | |
|---|---|---|
| 9,839,360 B2 | 12/2017 | Rebec et al. |
| 9,877,651 B2 | 1/2018 | Watson et al. |
| 10,019,555 B2 | 7/2018 | Manice et al. |
| 2011/0022916 A1* | 1/2011 | Desai ............... H04L 9/0662 714/748 |
| 2011/0213216 A1 | 9/2011 | McKenna et al. |
| 2012/0230234 A1* | 9/2012 | Kim .................. H04L 1/1854 370/310 |
| 2015/0090261 A1 | 4/2015 | Crosbie |
| 2016/0286543 A1 | 9/2016 | Putterman et al. |
| 2017/0109493 A1 | 4/2017 | Hogg et al. |
| 2017/0160111 A1* | 6/2017 | Dowdall ............. G01J 1/4204 |
| 2017/0296772 A1* | 10/2017 | Costella ............... A61M 11/06 |
| 2018/0004909 A1 | 1/2018 | Cronin et al. |
| 2018/0110078 A1* | 4/2018 | Mandapaka ......... H04B 17/318 |
| 2018/0140786 A1* | 5/2018 | Calderon Oliveras ................. A61M 15/0065 |
| 2018/0242130 A1* | 8/2018 | Ganton ................ H04W 4/06 |
| 2019/0102522 A1 | 4/2019 | Barrett et al. |

FOREIGN PATENT DOCUMENTS

| | | |
|---|---|---|
| WO | WO 2015/178907 A1 | 11/2015 |
| WO | WO 2016/097368 A1 | 6/2016 |
| WO | WO 2018/011113 A1 | 1/2018 |

OTHER PUBLICATIONS

Anonymous: "Bluetooth Low Energy—Wikipedia—Version of Mar. 18, 2018", Wikipedia, Mar. 18, 2018 (Mar. 18, 2018), XP055591863, Retrieved from the Internet: URL:https://en.wikipedia.org/w/i ndex.php?title=Bluetooth_Low_Energy&oldid=831059457 [retrieved on May 24, 2019], 13 pages.

United States Office Action, U.S. Appl. No. 15/940,950, dated Sep. 19, 2018, nine pages.

* cited by examiner

DECREASED LATENCY WIRELESS COMMUNICATION FOR USE WITH MEDICAMENT DEVICES

BACKGROUND

Field of Art

The disclosure relates generally to methods of improving communication of a client device and a medicament device sensor for detecting medicament usage, more specifically to wireless communications with reduced latency between pings between such devices.

Description of the Related Art

Asthma remains a significant and costly public health problem. Worldwide, the World Health Organization estimates the population with asthma may be 300 million, and predicts that it will rise to 400 million by 2025. In the United States, asthma affects 1 in 12 individuals in the U.S. and prevalence is on the rise, leading to more than $56 billion per year in health care utilization costs.

Despite the development of new medications, rates of hospitalizations and emergency room visits have not declined. Each year in the United States the disease causes approximately 2 million emergency department visits, 500,000 hospitalizations, and 5,000 deaths. In addition, asthma is responsible for an estimated 15 million missed days of school, and 12 million days of work. Total annual costs to US health insurers and employers are greater than $18 billion.

The majority of these exacerbations could be prevented with currently available treatments; however, only 1 in 5 asthmatics has the disease under control. Newly revised national guidelines urge doctors to more closely monitor whether treatment is controlling everyday symptoms and improving quality of life. Physicians, however, have few available tools to assess how well their patients are doing day-to-day. An increasing number of physicians have begun to use periodic, written questionnaires (such as the Asthma Control Test) to monitor patients and determine their level of control. These instruments require patients to accurately recall and report the frequency of symptoms, inhaler usage, and activity level and restriction over some period of time (usually two to four weeks). As a result, these questionnaires are subject to error introduced by biases (recall), different interpretations of symptoms, and behaviors (non-adherence), and only provide information at the time they are used.

More generally, medicament devices such as medical inhalers dispense corticosteroids which allow patients to manage respiratory symptoms such as constricted airflow. When patients use medicament devices, the ability to record instances of medication events and send recorded instances to physicians allows better monitoring of patients by physicians. A medicament device sensor attached to such medicament devices such as inhalers can aid in recording instances of medicament dispensing and transmitting the recorded instances to a server; however such events are generally reported much later than their time of occurrence, if at all. In some instances, such events are reported many hours if not days later, which is problematic.

SUMMARY

The present disclosure describes a computer-implemented method for updating a plurality of parameters on a medicament device sensor via a wireless connection by a client device. In one embodiment, the medicament device is a medical inhaler used to provide medicament doses through inhalation by a user. The client device stores the plurality of parameters for the medicament device sensor on the client device. The client device updates one or more parameters of the plurality of parameters on the client device. The client device receives a plurality of periodic chirps from the medicament device sensor, wherein the client device can establish a wireless connection with the medicament device sensor having received a chirp. A chirp is a small packet of data broadcast for a short duration of time indicating readiness to establish a wireless connection with the client device. After receiving a chirp, the client device forms the wireless connection between the medicament device sensor and the client device. And through the wireless connection, the client device transmits the updated one or more parameters of the plurality of parameters to the medicament device sensor. Power usage by the medicament device sensor depends in part on periodicity of chirps that the medicament device sensor broadcasts to the client device. In one embodiment, the wireless connection is a Bluetooth connection, specifically utilizing the Bluetooth Low Energy protocol. This embodiment of the computer-implemented method provides for improved efficiency in connection latency. The utilization of Bluetooth Low Energy broadcasting enables sending of small low-energy packets of data as chirps detailing availability of the medicament device sensor for pairing with the client device. The decrease in power usage per chirp enables decreasing a chirping interval thereby reducing temporal latencies when attempts are made to communicate with the medicament device sensor by the client device.

More frequent communication between the medicament device sensor and the client device provides increased feasibility of certain functions for the medicament device sensor. As described above, decreased latency in chirping interval with wireless connectivity provides quickened transfer of parameter updates to the medicament device sensor. In other scenarios, decreased latency in chirping interval with wireless connectivity aids in a feature for clients to locate the medicament device sensor through the client device. Likewise, offloading of medicament device sensor records improves with reduced latencies. These added features open up allocation of computing resources and reduce power consumption thus extending battery life of the medicament device sensor. These added features also provide increased user experience with decreased latency in connecting to the medicament device sensor through the client device.

The figures depict various embodiments of the presented invention for purposes of illustration only. One skilled in the art will readily recognize from the following discussion that alternative embodiments of the structures and methods illustrated herein may be employed without departing from the principles described herein.

DETAILED DESCRIPTION

I. System Environment

Figure 1:
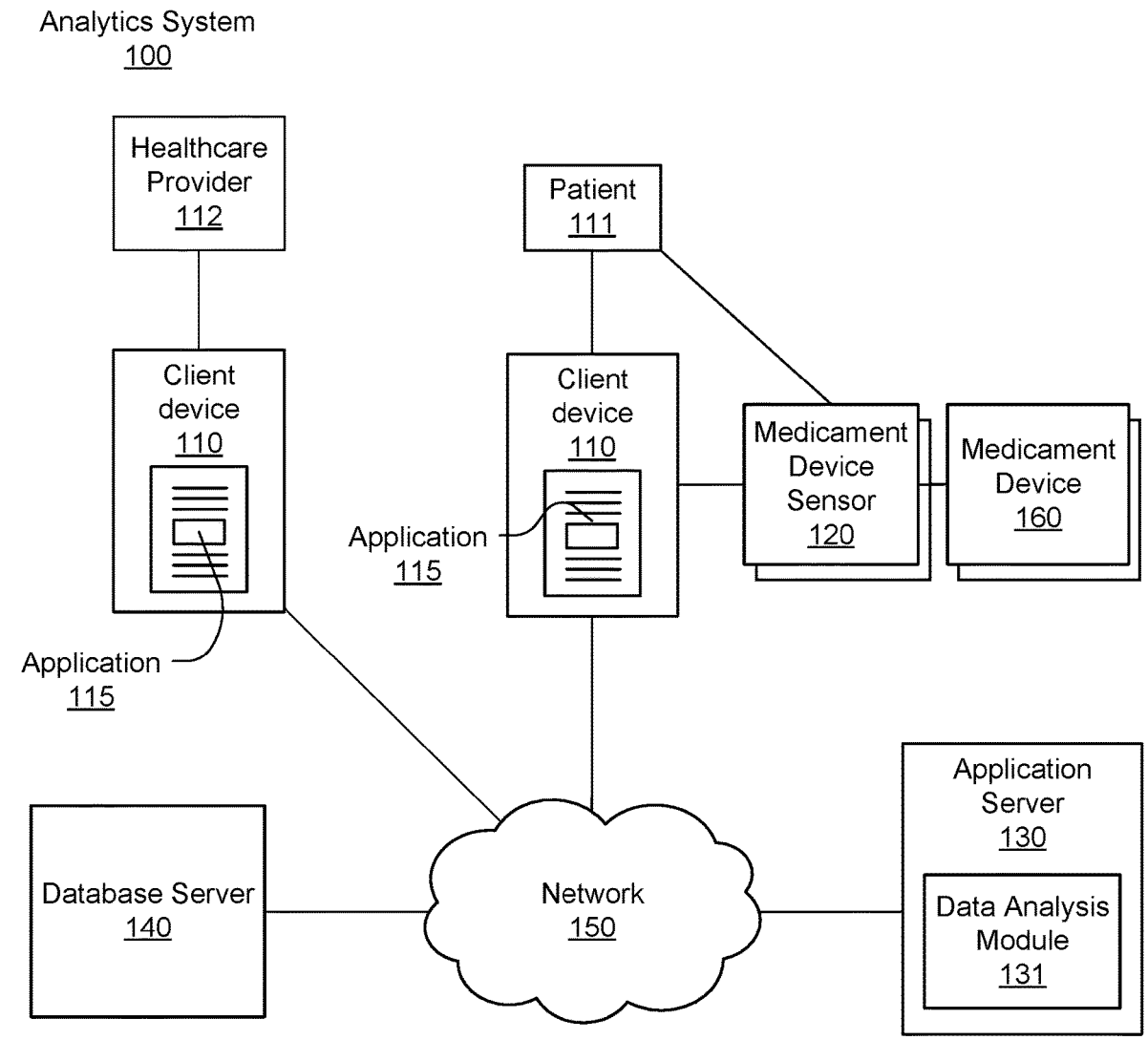
FIG. 1 shows an analytics system for monitoring accurate, real-time medicament device usage, performing analytics on that data, and providing notifications around medicament device events, according to one embodiment.

FIG. 1 shows an analytics system 100 for monitoring accurate, real-time medicament device usage, performing analytics on that data, and providing information about those events, according to one embodiment.

The analytics system includes client computing devices 110 (herein referred to as simply "client 110"), a medicament device sensor 120 (herein referred to as simply as "sensor 120"), a medicament device 160, an application server 130, a database server 140, and a network 150. Although FIG. 1 illustrates only a single instance of most of the components of the analytics system 100, in practice more than one of each component may be present, and additional or fewer components may be used in conjunction with the components shown.

I.A. Client and Application

The clients 110, at the behest of their users, interact with the analytics system 100 via the network 150. For purposes of explanation and clarity it is useful to identify at least two different types of users. A patient 111 is a user burdened with a medical challenge who makes use of the analytics system 100 at least in part to obtain personalized risk notifications provided by the server 130 based on records by the sensor 120. Records recorded by the sensor 120 may include rescue and controller events involving rescue and controller medicament dosages, respectively, by one or more medicament devices 160 (e.g., one for each type of medication). Such notifications can be provided in exchange for the user's permission to allow the analytics system 100 to monitor the patient's 111 medicament device 160 usage. As will be explained below, medication events are detected by a sensor 120 associated with the medicament device 160 and the user's client 110, which in turn reports to the application server 130, which in turn can initiate a process to generate notifications on the user's medical status as determined by the analytics system 100 which may be provided to the user through the client 110.

Another type of user is a healthcare provider 112 who, again with the patient's 111 express permission, also receives notifications regarding a patient's medicament management. In certain cases, the medicament device is a medical inhaler for providing medication, with some medication used for controlling asthma, chronic obstructive pulmonary disease, chronic sinusitis, allergies, another breathing challenge, etc. The patient 111 may also express permission for notifications to be shared with a community revolving around medicament usage event data and derived statistics regarding rescue events associated with medicament dosage and other associated data. Other types of users are also contemplated, such as parents/guardians of patients 111 who may also want to receive notifications in the event that their own clients 110 are distinct from that of their children.

The client 110 is a computer system. An example physical implementation is described more completely below with respect to FIG. 2. The client 110 is configured to wirelessly communicate with the analytics system 100 via network 150. With network 150 access, the client 110 transmits to the analytics system 100 the user's geographical location and the time of a rescue medication event, as well as information describing the event as received from the associated sensor 120.

Regarding user location and event times, the client 110 may determine the geographical location and time of a rescue event through use of information about the cellular or wireless network 150 to which it is connected. For example, the current geographical location of the client 110 may be determined by directly querying the software stack providing the network 150 connection. Alternatively, the geographical location information may be obtained by pinging an external web service (not shown in FIG. 1) made accessible via network 150. The time of an event can be provided by the sensor 120 as part of the event data or added to event data by querying an appropriate software routine available as part of the client's 110 native operating system.

In addition to communicating with the application server 130, clients 110 connected wirelessly to the analytics system 100 may also exchange information with other connected clients 110. For example, through a client software application 115, a healthcare provider 112 may receive a notification describing a recent rescue event about a patient 111, then in response send a recommendation to the patient 111 for post rescue event treatment. Similarly, through application 115 patients 111 may communicate with their healthcare providers 112 and other patients 111.

Application 115 provides a user interface (herein referred to as a "dashboard") that is displayed on a screen of the client 110 and allows a user to input commands to control the operation of the application 115. The dashboard is the mechanism by which healthcare providers 112 and patients 111 access the analytics system 100. For example, the dashboard allows patients 111 and providers 112 to interact with each other, receive rescue event risk notifications, exchange messages about treatment, provide and receive additional event and non-event data, and so on. Application 115 may be coded as a web page, series of web pages, or content otherwise coded to render within an internet browser. Application 115 may also be coded as a proprietary software program configured to operate on the native operating system of the client 110. The dashboard is more completely described below in conjunction with FIG. 3.

In addition to providing the dashboard, application 115 may also perform some data processing on rescue event data locally using the resources of client 110 before sending the processed data through the network 150. Event data sent through the network 110 is received by the application server 130 where it is analyzed and processed for storage and retrieval in conjunction with database server 140. The application server 130 may direct retrieval and storage request to the database system 130 as required by the client application 115.

The client 110 communicates with the sensor 120 using a network adapter and either a wired or wireless communication protocol, an example of which is the Bluetooth Low Energy (BTLE) protocol. BTLE is a short-ranged, low-powered, protocol standard that transmits data wirelessly over radio links in short range wireless networks. After the sensor 120 and client 110 have been paired with each other using a BTLE passkey, the sensor 120 automatically synchronizes and communicates information relating to medicament device 160 usage to the client 110. If the sensor 120 hasn't been paired with a client 110 prior to a rescue medication event, the information is stored locally until such a pairing occurs. Upon pairing, the sensor 120 communicates any stored event records to the client 110. In other implementations, other types of wireless connections are used (e.g., infrared or 802.11).

Although clients 110 and medicament devices 160 are described above as being separate physical devices (such as smart phones and inhalers, respectively), in the future it is contemplated the medicament devices 160 may include not only sensors 120 integrated into a single housing with the device 160, but also aspects of the client 110. For example, a medicament device 160 may include an audiovisual interface including a display or other lighting elements as well as speakers for presenting visual audible information. In such an implementation the medicament device 160 itself may present the contents of notifications provided by the server 130 directly, in place of or in addition to presenting them through the clients 110.

I.B. Medicament Device and Sensor

The medicament device 160 is a medical device used to deliver medication to the lungs of a user experiencing constricted respiratory airflow. Medicament devices (e.g. inhalers) are typically portable and small enough to be carried by hand for ease of accessibility when treating respiratory attacks. In one embodiment, medicine is delivered in aerosol form through a medicament device 160 such as a metered dose inhaler. Metered dose inhalers include a pressured propellant canister of aerosol medicine, a metering valve for delivering a regulated medicine dosage amount, and a plastic holder that holds the pressurized canister and also forms a mouthpiece for delivery of the medicine. In another embodiment, medicine is delivered in dry powder form through a medicament device 160 such as a dry powder inhaler. Dry powder inhalers may have Cartesian ovular shaped bodies that house wheel and gear mechanisms enabling a user to index through a strip of dry powder medication. The bodies of dry powder inhalers also include a manifold and a mouthpiece to deliver dry powder to the user. Single dose inhalers may operate similarly to the dry powder inhalers functionally providing a single dose of a medicament at a time. Examples of controller medications that are dispensed by a controller medicament device 160 include beclomethasone, budesonide, and fluticasone as well as combinations of those medications with a long-acting bronchodilator such as salmeterol or formoterol. Examples of rescue medications that are dispensed by a rescue medicament device 160 include albuterol, salbutamol, levalbuterol, metaproterenol, and terbutaline.

Each patient may be associated with more than one medicament device 160. For example, the patient may have a rescue medicament device 160 that dispenses rescue medication, and a controller medicament device 160 that dispenses controller medication. Similarly, each patient may be associated with more than one sensor 120, each chosen to operate with one of the patient's medicament devices 160.

Generally, a sensor 120 is a physical device that monitors the usage of the medicament dispenser 160. The sensor 120 is either removeably attachable to the medicament dispenser without impeding the operation of the medication dispenser, or the sensor 120 is an integrated component that is a native part of the medicament dispenser 160 as made available by its manufacturer.

The sensor 120 includes its own network adapter (not shown) that communicates with the client 110 either through a wired connection, or more typically through a wireless radio frequency connection. In one embodiment, the network adapter is a Bluetooth Low Energy (BTLE) wireless transmitter, however in other embodiments other types of wireless communication may be used (e.g., infrared, 802.11). An embodiment of the sensor 120 as a sensor to a medical inhaler communicating with an embodiment of the client 110 will be discussed further in conjunction with FIGS. 2-5.

The sensor 120 may also be configured to communicate more directly with the application server 130. For example, if the network adapter of the sensor 120 is configured to communicate via a wireless standard such as 802.11 or LTE, the adapter may exchange data with a wireless access point such as a wireless router, which may in turn communicate with the application server 130 without necessarily involving the client 110 in every exchange of data. These two methods of communicating are not mutually exclusive, and the sensor 120 may be configured to communicate with both the client 110 and the application server 130, for example using redundant transmission to ensure event data arrives at the application server 130 or to provide information directly to the client 110 while the application server 130 is determining what notification to provide in response to an event.

As introduced above, the sensor 120 captures data about usage of the medicament device 160. Specifically, each sensor 120 captures the time and geographical location of the rescue medication event, that is, usages of the rescue medicament device 160, by the patient 111. Each sensor 120 transmits the event data in real-time or as soon as a wireless connection is achieved, automatically without input from the patient 111 or health care provider 112. The medication event information is sent to the application server 130 for use in analysis, generation of rescue event notifications, and in aggregate analyses of event data across multiple patients.

To accomplish this goal, there are a number of different ways for the sensor 120 to be constructed, and in part the construction will depend upon the construction of the medicament device 160. Generally, all sensors 120 will include an onboard processor, persistent memory, and the network adapter mentioned above that together function to record, store, and report medication event information to the client 110 and/or server 130. Sensors 120 may also include a clock for recording the time and date of events and/or a Global Positioning System (GPS) receiver for recording GPS coordinates of the sensors 120.

Regarding specific sensor 120 constructions, traditional inhalers, such as mechanical dose counters, are not designed with sensors 120 in mind, and thus the sensor 120 may be constructed accordingly. Some implementations in this manner include mechanical, electrical, or optical sensors to detect movement of the device 160, priming of the device, activation of the device, inhalation by the user, etc. In contrast, modern inhalers, such as deflectable membrane dose counters, include electrical circuitry that may report event information as an electrical data signal which a sensor 120 is designed to receive and interpret, for example the medicament device 160 itself may report movement, priming, and activation to the sensor 120.

The sensor 120 may store parameters incorporated for use with recording medicament dosage events by the medicament device 160. Parameters are software, firmware, or hardware data that control settings or specific instruction sets to be carried out by the computing architecture of the medicament device 160. Example parameters include, but are not limited to: (i) medicament dosage reminder times, delays, or other similar settings, (ii) personalized audio ringtones for playback on an audio speaker of a medicament device, in some instances in association with particular device functions, (iii) software instructions for controlling the operation of the sensor 120 function, (iv) calibration and configuration values for sensing and output components, and (v) unique device identifiers, authentication keys, and encryption keys. Some or all of the parameters of the sensor 120 may be stored in the client 110. The client 110 communicates with the sensor 120 when parameters are updated, so that the client 110 can transmit the updated parameters for storage within and use by the sensor 120.

More information regarding hardware and software components for the sensors 120 and medicament devices 160, as well as the interaction between them to record rescue medication events can be found in U.S. patent application Ser. No. 12/348,424, filed Jan. 1, 2009, and International Application No. PCT/US2014/039014, filed May 21, 2014, both of which are incorporated by reference herein in their entirety.

I.C. Application Server

Figure 2:
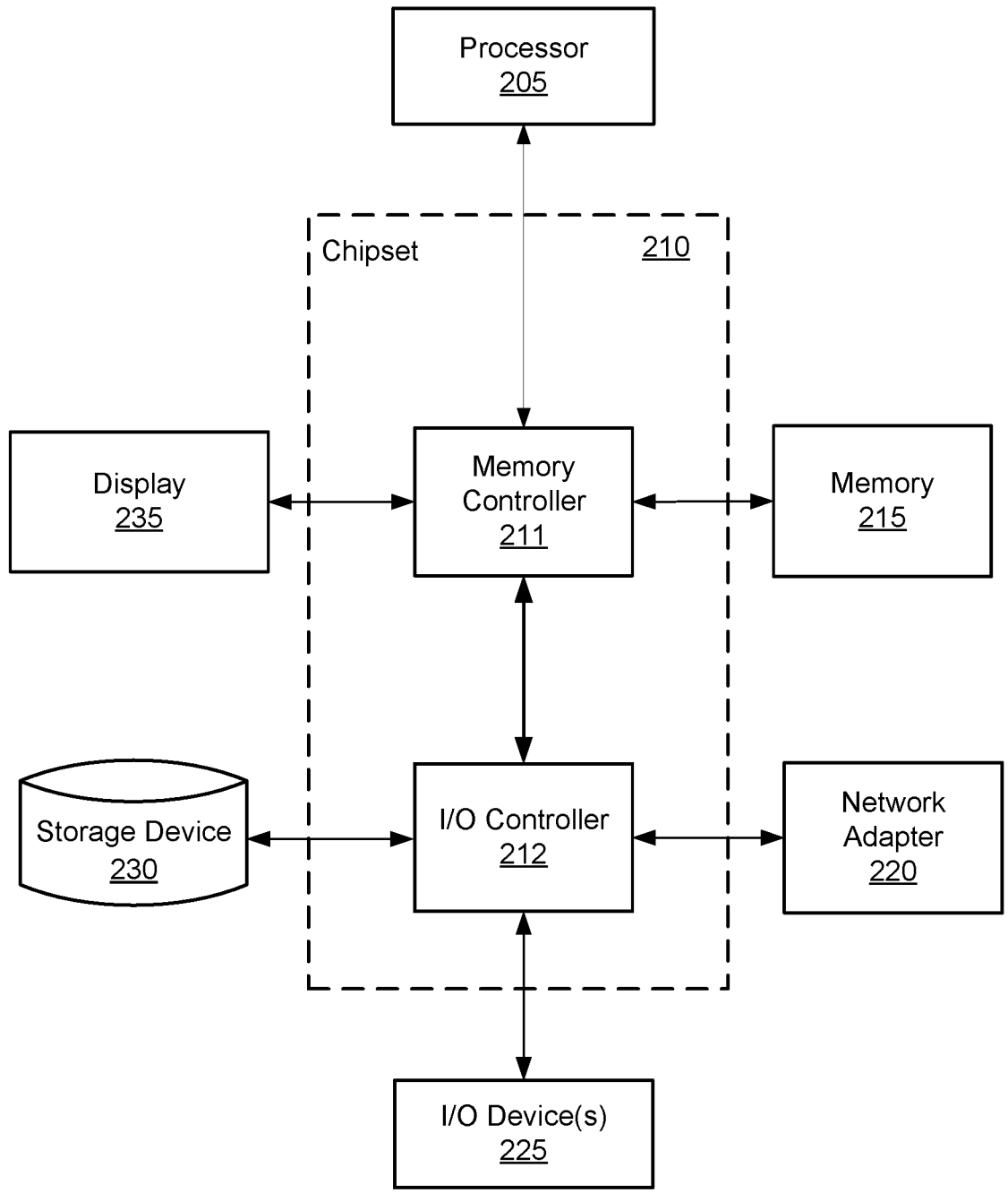
FIG. 2 is a high-level block diagram illustrating an example computing device used either as a client device, application server, and/or database server, according to one embodiment.

The application server 130 is a computer or network of computers. Although a simplified example is illustrated in FIG. 2, typically the application server will be a server class system that uses powerful processors, large memory, and faster network components compared to a typical computing system used, for example, as a client 110. The server typically has large secondary storage, for example, using a RAID (redundant array of independent disks) array and/or by establishing a relationship with an independent content delivery network (CDN) contracted to store, exchange and transmit data such as the asthma notifications contemplated above. Additionally, the computing system includes an operating system, for example, a UNIX operating system, LINUX operating system, or a WINDOWS operating system. The operating system manages the hardware and software resources of the application server 130 and also provides various services, for example, process management, input/output of data, management of peripheral devices, and so on. The operating system provides various functions for managing files stored on a device, for example, creating a new file, moving or copying files, transferring files to a remote system, and so on.

The application server 130 includes a software architecture for supporting access and use of analytics system 100 by many different clients 110 through network 150, and thus at a high level can be generally characterized as a cloud-based system. The application server 130 generally provides a platform for patients 111 and healthcare providers 112 to report data recorded by the sensors 120 associated with their medicament devices 160 including both rescue medication and controller medication events, collaborate on medication treatment plans, browse and obtain information relating to their condition and geographic location, and make use of a variety of other functions.

Generally, the application server 130 is designed to handle a wide variety of data. The application server 130 includes logical routines that perform a variety of functions including checking the validity of the incoming data, parsing and formatting the data if necessary, passing the processed data to a database server 140 for storage, and confirming that the database server 140 has been updated.

The application server 130 stores and manages data at least in part on a patient by patient basis. Towards this end, the application server 130 creates a patient profile for each user. The patient profile is a set of data that characterizes a patient 111 of the analytics system 100. The patient profile may include identifying information about the patient such as age, gender, current rescue medication, current controller medication, notification preferences, a controller medication adherence plan, a patient's relevant medical history, and a list of non-patient users authorized to access the patient profile. The profile may further specify a device identifier, such as a unique media access control (MAC) address identifying the one or more clients 110 or sensors 120 authorized to submit data (such as controller and rescue medication events) for the patient.

The profile may specify which different types of notifications are provided to patients 111 and their personal healthcare providers 112, as well as the frequency with which notifications are provided. For example, a patient 111 may authorize a healthcare provider 112 to receive notifications indicating a rescue event. The patient 111 may also authorize their healthcare provider 112 be given access to their patient profile and rescue event history. If the healthcare provider 112 is provided access to the patient profile of the patient 111, the healthcare provider may specify controller adherence or rescue medication plans. Medication plans may include a prescribed number of doses per day for controller medications.

The application server 130 also creates profiles for health care providers 112. A health care provider profile may include identifying information about the health care provider 112, such as the office location, qualifications and certifications, and so on. The health care provider profile also includes information about their patient population. The provider profile may include access to all of the profiles of that provider's patients, as well as derived data from those profiles such as aggregate demographic information, rescue and controller medication event patterns, and so on. This data may be further subdivided according to any type of data stored in the patient profiles, such as by geographic area (e.g., neighborhood, city) or by time period (e.g., weekly, monthly, yearly).

The application server 130 receives rescue medication event information from the client 110 or the sensor 120, triggering a variety of routines on the application server 130. In the example implementations described below, the data analysis module 131 executes routines to access asthma event data as well as other data including a patient's profile, analyze the data, and output the results of its analysis to both patients 111 and healthcare providers 112. This process is generally referred to as an asthma risk analysis. The asthma risk analysis may be performed at any point in time, in response to a rescue event, due to a relevant change in the patient's environment, and in response to any one of a number of triggering conditions discussed further below.

Other analyses are also possible. For example, a risk analysis may be performed on rescue and controller medication use for multiple patients to identify based on spatial/temporal clusters (or outbreaks) of medication use based on historically significant permutations from individual, geographic, clinical, epidemiologic, demographic, or spatial or temporal baselines or predicted or expected values. Other types of analyses may include daily/weekly adherence trends, adherence changes over time, adherence comparisons to other relevant populations (e.g., all patients, patients on a particular rescue medication or controller medication or combination thereof, identification of triggers (spatial, temporal, environmental), rescue use trends over time, and rescue use comparisons to other relevant populations.

Responsive to any analyses performed, the application server 130 prepares and delivers push notifications to send to patients 111, authorized healthcare providers 112, and/or other users provided access to the patient's profile. Notifications can provide details about the timing, location, and affected patient(s) 111 involved in a medication rescue event. Notifications may additionally comprise a distress or emergency signal that requests emergency assistance that is distributed to emergency assistance providers 112. Notifications may also include the results of the asthma risk analysis performed by the data analysis module 131. More information regarding the types of notifications that may be sent and the content they may contain is further described below.

In addition to providing push notifications in response to an asthma risk analysis, notifications may also be provided as pull notifications, at particular time intervals. Additionally, some notifications (whether push or pull) may be triggered not in response to an asthma risk analysis performed in response to a rescue medication event, but instead in response to a risk analysis performed in response to one of the underlying factors in the asthma risk analysis changing, such that an updated notification is warranted. For example, if weather conditions indicate that an increase in air pollution is occurring or is imminent, this may trigger the carrying out of asthma risk analyses for all patients located in the particular geographic area where the pollution is occurring.

Notifications are provided through the network 150 to client applications 115 in a data format specifically designed for use with the client applications, and additionally or alternatively may be provided as short message service (SMS) messages, emails, phone calls, or in other data formats communicated using other communication mediums.

I.D. Database Server

The database server 140 stores patient and provider related data such as profiles, medication events, patient medical history (e.g., electronic medical records). Patient and provider data is encrypted for security and is at least password protected and otherwise secured to meet all Health Insurance Portability and Accountability Act (HIPAA) requirements. Any analyses (e.g., asthma risk analyses) that incorporate data from multiple patients (e.g., aggregate rescue medication event data) and are provided to users is de-identified so that personally identifying information is removed to protect patient privacy.

The database server 140 also stores non-patient data used in asthma risk analyses. This data includes regional data about a number of geographic regions such as public spaces in residential or commercial zones where patients are physically located and may be exposed to pollutants. This data may specifically include or be processed to obtain a patient's proximity to green space (areas including concentrated numbers of trees and plants). One example of regional data includes georeferenced weather data, such as temperature, wind patterns, humidity, the air quality index, and so on. Another example is georeferenced pollution data, including particulate counts for various pollutants at an instance of time or measured empirically. The regional data includes information about the current weather conditions for the time and place of the rescue event such as temperature, humidity, and air quality index. All of the items of data above may vary over time, and as such the data itself may be indexed by time, for example separate data points may be available by time of day (including by minute or hour), or over longer periods such as by day, week, month, or season. Although the database server 140 is illustrated in FIG. 1 as being an entity separate from the application server 130 the database server 140 may alternatively be a hardware component that is part of another server such as server 130, such that the database server 140 is implemented as one or more persistent storage devices, with the software application layer for interfacing with the stored data in the database is a part of that other server 130.

The database server 140 stores data according to defined database schemas. Typically, data storage schemas across different data sources vary significantly even when storing the same type of data including cloud application event logs and log metrics, due to implementation differences in the underlying database structure. The database server 140 may also store different types of data such as structured data, unstructured data, or semi-structured data. Data in the database server 140 may be associated with users, groups of users, and/or entities. The database server 140 provides support for database queries in a query language (e.g., SQL for relational databases, JSON NoSQL databases, etc.) for specifying instructions to manage database objects represented by the database server 140, read information from the database server 140, or write to the database server 140.

I.E. Network

The network 150 represents the various wired and wireless communication pathways between the client 110 devices, the sensor 120, the application server 130, and the database server 140. Network 150 uses standard Internet communications technologies and/or protocols. Thus, the network 150 can include links using technologies such as Ethernet, IEEE 802.11, integrated services digital network (ISDN), asynchronous transfer mode (ATM), etc. Similarly, the networking protocols used on the network 150 can include the transmission control protocol/Internet protocol (TCP/IP), the hypertext transport protocol (HTTP), the simple mail transfer protocol (SMTP), the file transfer protocol (FTP), etc. The data exchanged over the network 150 can be represented using technologies and/or formats including the hypertext markup language (HTML), the extensible markup language (XML), JavaScript Object Notation (JSON), etc. In addition, all or some links can be encrypted using conventional encryption technologies such as the secure sockets layer (SSL), Secure HTTP (HTTPS) and/or virtual private networks (VPNs). In another embodiment, the entities can use custom and/or dedicated data communications technologies instead of, or in addition to, the ones described above.

II. Example Computing Devices

FIG. 2 is a high-level block diagram illustrating physical components of an example computer 200 that may be used as part of a client 110, application server 130, and/or database server 140 from FIG. 1, according to one embodiment. Illustrated is a chipset 210 coupled to at least one processor 205. Coupled to the chipset 210 is volatile memory 215, a network adapter 220, an input/output (I/O) device(s) 225, a storage device 230 representing a non-volatile memory, and a display 235. In one embodiment, the functionality of the chipset 210 is provided by a memory controller 211 and an I/O controller 212. In another embodiment, the memory 215 is coupled directly to the processor 205 instead of the chipset 210. In some embodiments, memory 215 includes high-speed random access memory (RAM), such as DRAM, SRAM, DDR RAM or other random access solid state memory devices.

The storage device 230 is any non-transitory computer-readable storage medium, such as a hard drive, compact disk read-only memory (CD-ROM), DVD, or a solid-state memory device. The memory 215 holds instructions and data used by the processor 205. The I/O device 225 may be a touch input surface (capacitive or otherwise), a mouse, track ball, or other type of pointing device, a keyboard, or another form of input device. The display 235 displays images and other information from the computer 200. The network adapter 220 couples the computer 200 to the network 150.

As is known in the art, a computer 200 can have different and/or other components than those shown in FIG. 2. In addition, the computer 200 can lack certain illustrated components. In one embodiment, a computer 200 acting as server 140 may lack a dedicated I/O device 225, and/or display 218. Moreover, the storage device 230 can be local and/or remote from the computer 200 (such as embodied within a storage area network (SAN)), and, in one embodiment, the storage device 230 is not a CD-ROM device or a DVD device.

Generally, the exact physical components used in a client 110 will vary in size, power requirements, and performance from those used in the application server 130 and the database server 140. For example, clients 110, which will often be home computers, tablet computers, laptop computers, or smart phones, will include relatively small storage capacities and processing power, but will include input devices and displays. These components are suitable for user input of data and receipt, display, and interaction with notifications provided by the application server 130. In contrast, the application server 130 may include many physically separate, locally networked computers each having a significant amount of processing power for carrying out the asthma risk analyses introduced above. In one embodiment, the processing power of the application server 130 provided by a service such as Amazon Web Services™. Also in contrast, the database server 140 may include many, physically separate computers each having a significant amount of persistent storage capacity for storing the data associated with the application server.

As is known in the art, the computer 200 is adapted to execute computer program modules for providing functionality described herein. A module can be implemented in hardware, firmware, and/or software. In one embodiment, program modules are stored on the storage device 230, loaded into the memory 215, and executed by the processor 205.

III. Dashboard

Figure 3:
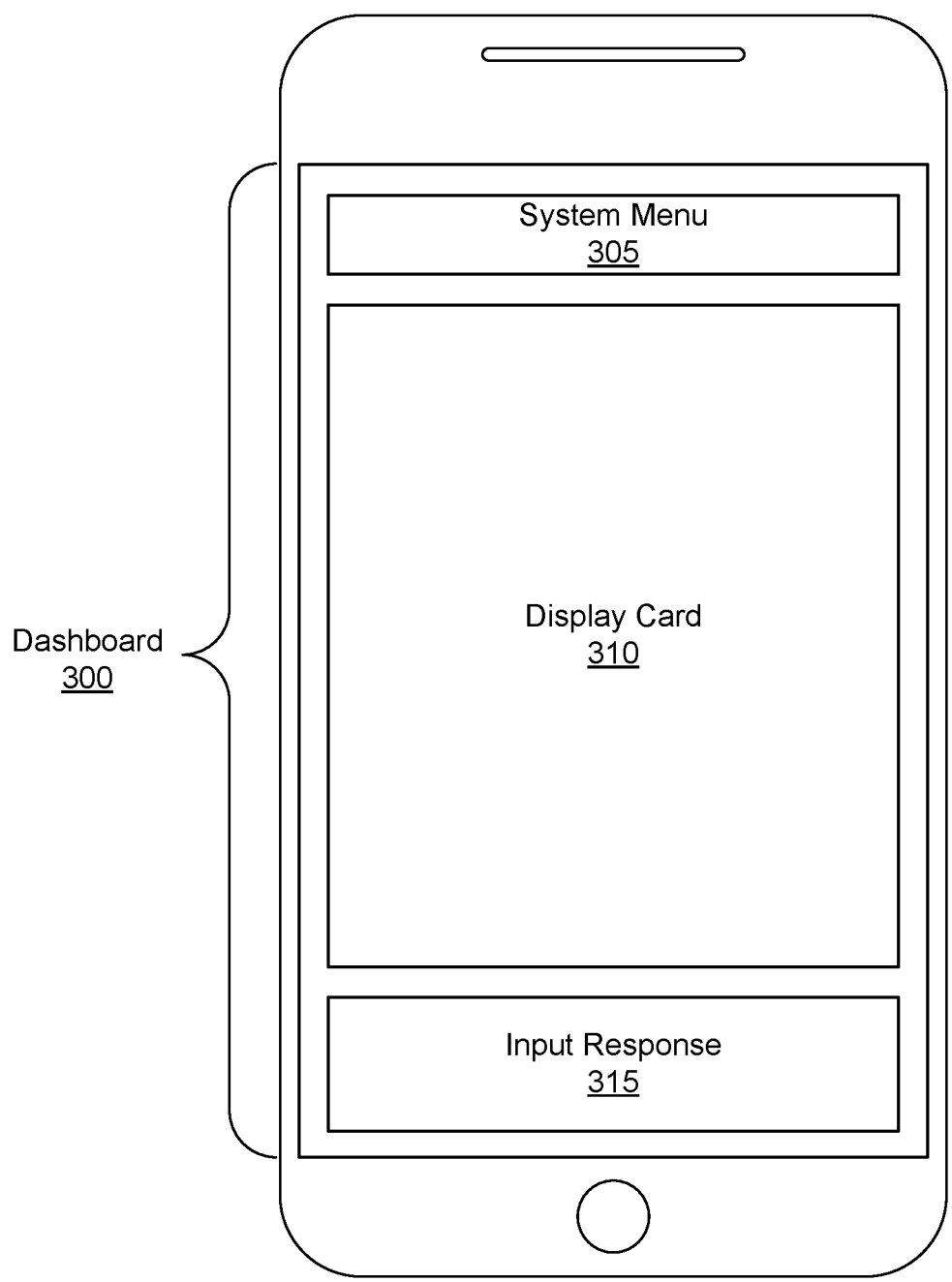
FIG. 3 is a graphical user interface of a client application that provides inputs and/or outputs from a user to an asthma analytics system, according to one embodiment.

The dashboard, for example dashboard 300 illustrated in FIG. 3, allows users to interact with the analytics system 100. The dashboard 300 provides a means to transfer information on a user-to-user (e.g., patient 111 to healthcare provider 112) or user-to-system/system-to-user basis. Dashboards 300 are accessed through the client application 115 on the client 110 and provide a mechanism for both patients and healthcare providers to monitor medication rescue events, exchange personalized patient healthcare information, and receive notifications such as rescue event risk notifications. Patients 111 may communicate with other healthcare providers 112 and other patients 111 through the dashboard 300, for example, to discuss and share information about breathing challenges, medication usage, or breathing challenge management. The ability to share healthcare information may give patients or healthcare care providers experiencing a similar issue a way to share individual perspectives.

The dashboard 300 also allows authorized healthcare providers 112 to access a list of patients to view, annotate, update, interact with, and export information about patient and community data and statistics in various demographics or geographic segments. Using the dashboard 300, healthcare providers are able to monitor patients 111 individually or in aggregate, to receive and provide feedback on how their associated patient populations are responding to breathing challenge management guidance. A healthcare provider 112 who has access to individual or multiple patients 111 has the ability to establish notification thresholds, set parameters for the notifications, and receive notifications when patients' 111 event history matches certain conditions (e.g. rescue event). Additionally, the dashboard 300 can receive and display regular reports of event patterns for specific demographics generated by the analytics system 100.

The dashboard 300 presents a variety of information including tabular data, graphical visualizations, and analyses to users through display "cards" 310. Display cards 310 are conformably suited to smaller displays typical of portable clients 110, for example mobile phones or tablets, and include "bite size" pieces of information that mimic the simplistic organizational style found in baseball cards. The dashboard 300 may also include a system menu 305 that allows users to navigate through different categories of healthcare information.

Notifications provided by the application server 130 are related to the display cards 310. Generally, notifications include not only information to be presented to the user through the application 115, but also parameters for specifying which display card 310 is to be used to display the contents of the notification. Any information pushed/pulled from the application server 130 may be associated with one or more cards. For example, a notification can be pushed to the patient based on the outcome of an risk analysis. The dashboard 300 will process the notification and determine which card/s to use to present the information in the notification. Continuing the example, the recipient of the notification may make a request to pull data from the application server 130. The application server 130 provides the requested data in another notification, and the dashboard 300 then determines which display card 310 to display the requested information.

The dashboard 300 may provide a variety of different display cards 310, which may be organized into categories. An information card type includes cards that display data. Information cards may, for example, display medication rescue events, statistics, and maps including both patient data and community data. Information cards are further sub-categorized into event, trend, education, and alert display cards.

Event cards include data relating to rescue medication events, such as a list of historical medication rescue events for a specific patient, or patient rescue event data overlaid on a geographical map for a specific provider.

IV. Chirping Interval in Client/Device Communications

Figure 4:
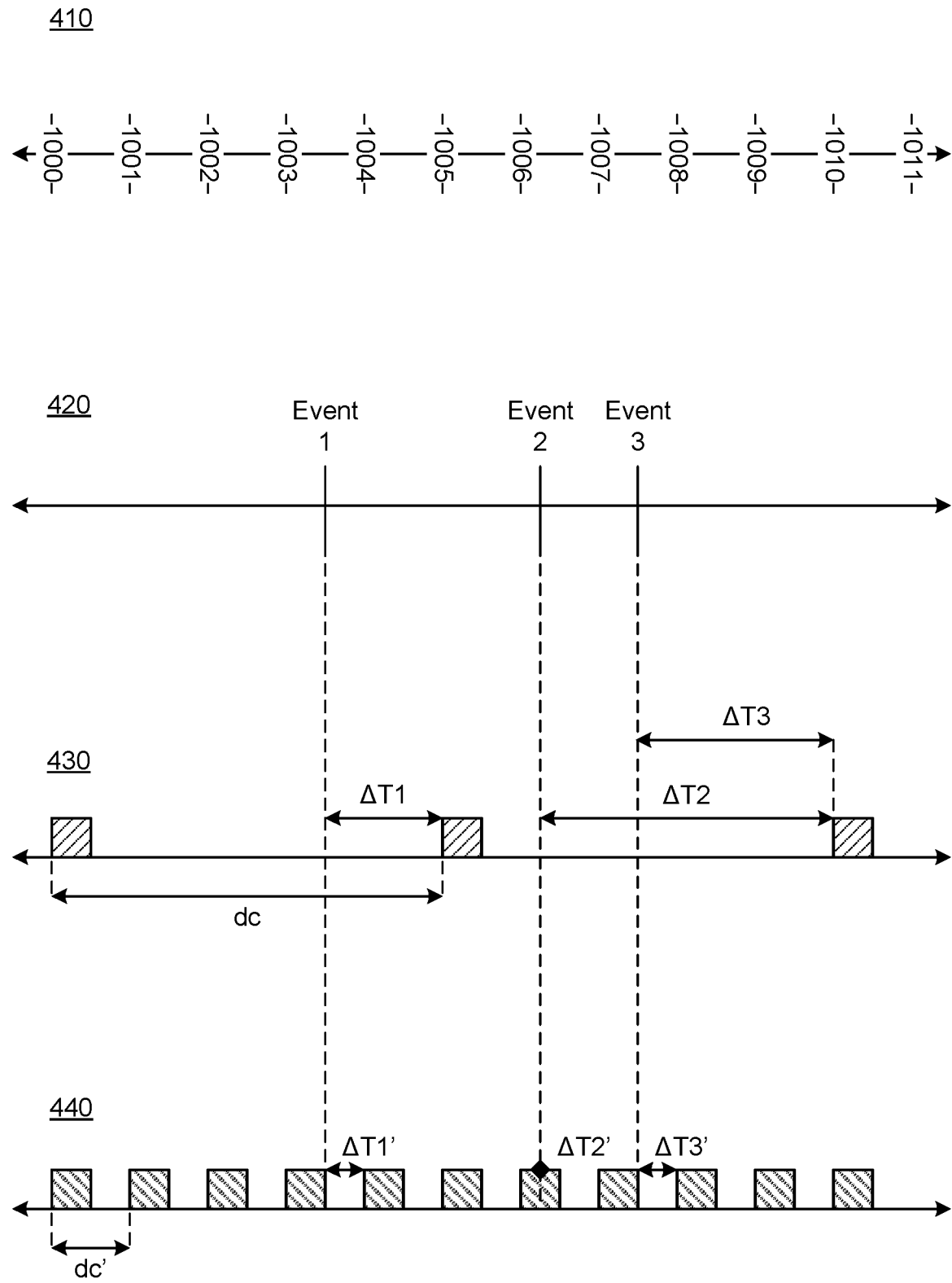
FIG. 4 is a set of timelines illustrating chirping intervals with transmitting events from a medicament device sensor to a client device, in accordance with an embodiment.

FIG. 4 is a set of example timelines illustrating a decreased latency in chirping interval with transmitting events from a medicament device sensor 120 (sensor 120) to a client device 110 (client 110), in accordance with an embodiment.

A first timeline 410 marks an example temporal resolution. An event timeline 420 denotes instances of recorded events by the sensor 120. An event may be a medicament dosage by the medicament device 160 as recorded by the sensor 120. Although the sensor 120 records the events, the sensor 120 must communicate with the client 110 to establish a connection for transmitting the recorded events. This is because no connection is assumed to exist between the client 110 and the sensor 120 at any given point in time, as this would needlessly consume power from the sensor 120 and further the sensor 120, may at any given point in time, be out of physical range of the client 110, such that no such connection could be formed. Instead, the client 110 waits for a chirp by the sensor 120 before initiating the connection, thereby providing a connection through which the sensor 120 may transmit the recorded events to the client 110. A chirp by the sensor 120 broadcasts readiness to establish a wireless connection with the client 110.

The first 430 and second 440 connection timelines demonstrates periodic chirping with a first and a second interval, respectively, where the second interval is smaller than that of the first interval.

The first timeline 410 marks out evenly spaced periods of time. For example, a first tick labeled 1000 of the plurality of ticks represents 10:00 AM with each tick denoting another minute. Although this example illustrates a temporal resolution in the order of minutes; the chirping interval of the sensor 120 is not limited to this temporal resolution as will be further discussed below.

Event timeline 420 denotes instances of recorded events by the sensor 120 to be transmitted to the client 110. In this illustrative event timeline 420, the sensor 120 has a total of 3 instances of recorded events—Event 1, Event 2, and Event 3. Event 1 occurs at 10:03.50 AM; Event 2 occurs at 10:06.25; Event 3 occurs at 10:07.50.

The first connection timeline 430 reveals periodic chirping of the sensor 120 providing for a wireless connection to be established with the client 110 every 5 minutes. The first chirping interval is denoted as dc between the start of two adjacent chirps. Each chirp of the periodic chirping has a duration of 0.5 minutes. From when Event 1 is recorded until its transmission during a connection formed after a chirp is denoted as a first temporal latency ($\Delta T1$) associated with Event 1. Similarly there's a second temporal latency ($\Delta T2$) and a third temporal latency ($\Delta T3$) associated with Event 2 and Event 3, respectively. In this example $\Delta T1$ is 1.5 minutes; $\Delta T2$ is 3.75 minutes; $\Delta T3$ is 2.5 minutes. The client 110 updates its stored parameters for the sensor 120 at Event 3 prior to transmitting Event 2 to the sensor 120. Thus in circumstances where the sensor 120 records multiple events within a short period of time, the sensor 120 would have a queue of recorded events to be transmitted to the client 110.

The second connection timeline 440 reveals periodic chirping of the sensor 120 providing for a Bluetooth connection to be established with the client 110 every 1 minute. The second chirping interval is denoted as dc'. Each chirp of the periodic chirping has a duration of 0.5 minutes. From when Event 1 is recorded until its transmission during a connection formed after a chirp is denoted as an improved first temporal latency ($\Delta T1'$). Similarly there is an improved second temporal latency ($\Delta T2'$) and an improved third temporal latency ($\Delta T3'$) for Event 2 and Event 3, respectively. In this example $\Delta T1'$ is 0.5 minutes; $\Delta T2'$ is 0 minutes; $\Delta T3'$ is 0.5 minutes. Compared to the temporal latencies from the first connection timeline 430, there is an improvement with 1 minute for Event 1, 3.75 minutes for Event 2, and 2 minutes for Event 3, averaging out to be a 2 minute average reduction in latency. Another difference from the first connection timeline 430 is that the second connection timeline 440 transmits each recorded event update prior to recording another event by the sensor 120. Generally there is an overall improvement of reducing latency between a recording of an event to sending the recorded event to the client 110. This also reduces volume of queues if multiple events are recorded prior to transmission to the client 110. This reduction in volume of queues frees up computing memory of the sensor 120. However, another consideration arises with decreasing chirping interval which is an increase in power due to increased chirping over a duration of time.

The catalyst for decreasing chirping interval while maintaining power feasibility is performing the chirping with a low energy use wireless standard such as Bluetooth Low Energy™ (BTLE), or another similar standard such as ANT™ or ANT+™ by ANT Wireless, near-field communication (NFC), Wi-Fi, etc, which allows for reducing processing power. In such an implementation, the sensor 120 broadcasts a chirp being a small packet advertising itself as available for connecting. In some embodiments, the small packet comprises at least a Generic Access Profile (GAP) and device information. The GAP describes the sensor 120 name with a sensor 120 identifier, such as a unique media access control (MAC) address (e.g., Propeller XX:XX:XX, where XX:XX:XX are last 3 octets of MAC address).

The device information may include many commonly needed characteristics helping describe the device such as firmware revision, model number, etc. For example, a plethora of different sensor 120s can all pair with the client 110 such that each sensor 120 has a specific model number for distinguishing from other sensor 120s. The small packet could consume around 0.01-0.50 Watts of battery power from the sensor 120 for transmitting a single chirp. This is compared to classic power consumption for prior power standards such as Bluetooth™, which would require at least 1 Watt per chirp. Lower power chirping, as demonstrated in FIG. 4, allows for greatly reduced temporal latencies in communications between the sensor 120 and the client 110 in a feasible way with respect to power consumption.

The chirping interval can be on the order of minutes, seconds (s), centiseconds (cs), or milliseconds (ms). For example, the chirping interval can be 1 ms, 5 ms, 1 cs, 5 cs, 10 cs, 50 cs, 1 s, 5 s, 10 s, 30 s, or 1 minute. Generally, the chirping interval is held constant; however, the sensor 120 may have multiple chirping intervals for use for varying circumstances, such as during different portions of each day. For example, during daytime, the chirping interval may be on the order of milliseconds, whereas during nighttime, the chirping interval may be on the order of minutes or seconds. In some instances, the chirping interval can be adjusted based on likelihoods of medicament events during different portions of the day. In another implementation, the chirping interval helps in reducing latency in transmitting parameter updates from the client 110 to the sensor 120. Thus having a longer chirping interval during nighttime assumes that a user would be less likely to transmit parameter updates at night.

These concepts are extendable to other possible assumptions about when more frequent or less frequent chirping would be beneficial. For example, chirping interval may be set to be shorter any time medicament events are more likely to be predicted to occur, such as based on weather, pollen, pollution, location, or other information, and accordingly set to be longer whenever medicament events are less likely to be predicted to occur. Details of predicting risk notification based on various factors can be found in U.S. patent application Ser. No. 15/724,968, incorporated by reference herein. More generally, the chirping interval may be dynamic based on any of these factors, or updated by updating the parameters of the sensor 120, as described herein.

The ability for the reduced latency in forming wireless connections provided by more frequent chirping between the sensor 120 and the client 110 provide increased feasibility of certain functions for the sensor 120. In one embodiment, the reduced latency in forming wireless connections provided by more frequent chirping reduces potential queues or backlogs of events to be reported, parameters to be updated, and/or a medicament device locating protocol. Regarding medicament device locating, the reduced latency in forming wireless connections provided by more frequent chirping provides a feature for clients to locate the medicament device through the client 110. These added features open up allocation of processing resources and reduce power consumption thus allowing for more efficient use of processing power by the sensor 120. These added features also provide increased user experience with the reduced latency in interactions with the sensor 120.

Applications of chirping will be described in greater detail in regards to FIGS. 5-8.

Figure 5:
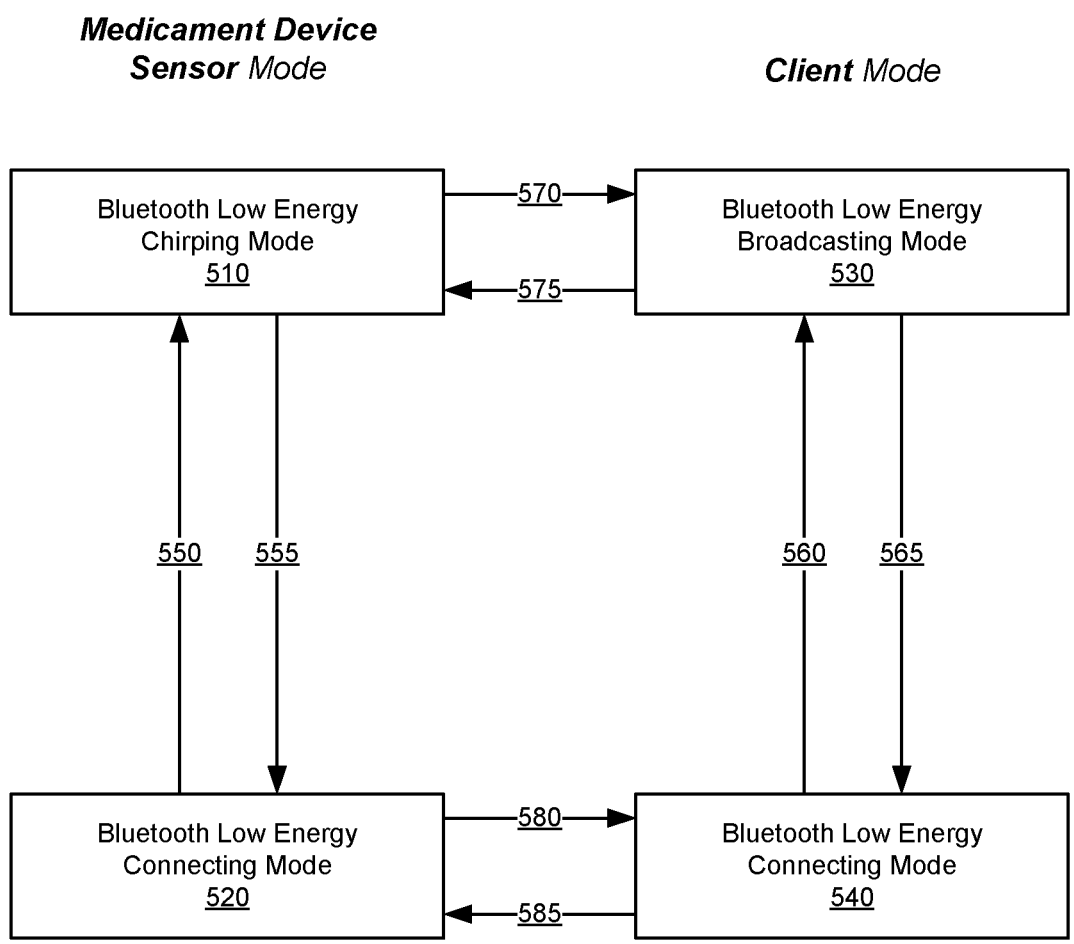
FIG. 5 is a flowchart describing a medicament device sensor and a client device Bluetooth modes, according to one embodiment.

FIG. 5 is a flowchart describing a medicament device sensor 120 (sensor 120), a client device 110 (client 110), and wireless connection modes, according to one embodiment. As above, the sensor 120 may be used as an attachment in association with an inhaler-type medicament device 160 such as a single dose inhaler or a metered dose inhaler (MDI). The sensor 120 records events such as medicament dispensing by the medicament device 160. The client 110 runs application 115 to communicate with the sensor 120. Among other functions, the application 115 is configured to use the client 110 to communicate parameter updates, or to request location information from the sensor 120. These examples will be discussed further in regards to FIGS. 6-8. The sensor 120 has a wireless chirping mode 510, similar to that described in FIG. 4, and a wireless connecting mode 520. The client 110 has a wireless broadcasting mode 530 and a wireless connecting mode 540. The sensor 120 or the client 110 can transition between wireless modes when occasions arise for data transfer between the two devices. In FIG. 5, the various wireless modes of the sensor 120 and the client 110 utilize Bluetooth Low Energy protocol, but in other embodiments low-energy wireless communication standards may be implemented.

The sensor 120's Bluetooth Low Energy chirping mode 510 broadcasts or chirps 570 periodically with low energy packets to notify a client 110 of connection availability. This lower power chirping mode 510 may be as demonstrated in FIG. 4, according to one embodiment.

The client 110's Bluetooth Low Energy broadcasting mode 530 receives chirps 570 from the sensor 120. In the client 110's Bluetooth Low Energy broadcasting mode 530, the client 110 receives chirps 570 from the sensor 120 periodically. The client 110 transmits a connection request 575 when the client 110 has data to transfer to the sensor 120.

The sensor 120's Bluetooth Low Energy connecting mode 520 and the client 110's Bluetooth Low Energy connecting mode 540 allow Bluetooth Low Energy connecting of the two devices. The sensor 120 and the client 110 are connected by their corresponding low power connecting modes 520 and 540, respectively, the two devices can transfer larger data packets back and forth. As mentioned in conjunction with FIG. 1, connecting of the two devices prior to data transfer can include a password exchange or authentication process. As will be described further in FIGS. 6-8, the sensor 120 transmits 580 recorded events, location information, and any other information to the client 110 and the client 110 transmits 585 parameter updates or location requests to the sensor 120.

The sensor 120 switches between its Bluetooth Low Energy chirping 510 and its Bluetooth Low Energy connecting mode 520 so as to efficiently allocate power usage. In practice, the sensor 120 will remain in the Bluetooth Low Energy chirping mode 510 for most of the time to reduce overall power usage. When the sensor 120 records an event, the sensor 120 can switch 550 to its Bluetooth Low Energy connecting mode 520 for establishing a connection with the client 110 for offloading recorded events, further described in conjunction with FIG. 8. Once recorded events are offloaded to the client 110, the sensor 120 can revert 555 back to its Bluetooth Low Energy chirping mode 510. In a similar fashion, the sensor 120 may receive a connection request 575 from the client 110 which causes the sensor 120 to switch 550 to its Bluetooth Low Energy connecting mode 520. In its Bluetooth Low Energy connecting mode 520, the sensor 120 can transmit requested information 585. Upon completion of tasks requested by the client 110, the sensor 120 can revert 555 back to its Bluetooth Low Energy chirping mode 510.

In a complementary fashion, the client 110 switches between its Bluetooth Low Energy broadcasting mode 530 and its Bluetooth Low Energy connecting mode 540 so as to efficiently allocate power usage. From the Bluetooth Low Energy broadcasting mode 530, the client 110 can switch 565 to its Bluetooth Low Energy connecting mode 540 when the sensor 120 has recorded events to offload. Similarly if the client 110 requests a connection with the sensor 120, the client 110 can also switch 565 to its Bluetooth Low Energy connecting mode 540 to transmit further requests or parameter updates to the sensor 120. After completion of transmission and receipt, the client 110 can revert 565 back to its Bluetooth Low Energy broadcasting mode 530.

Figure 6:
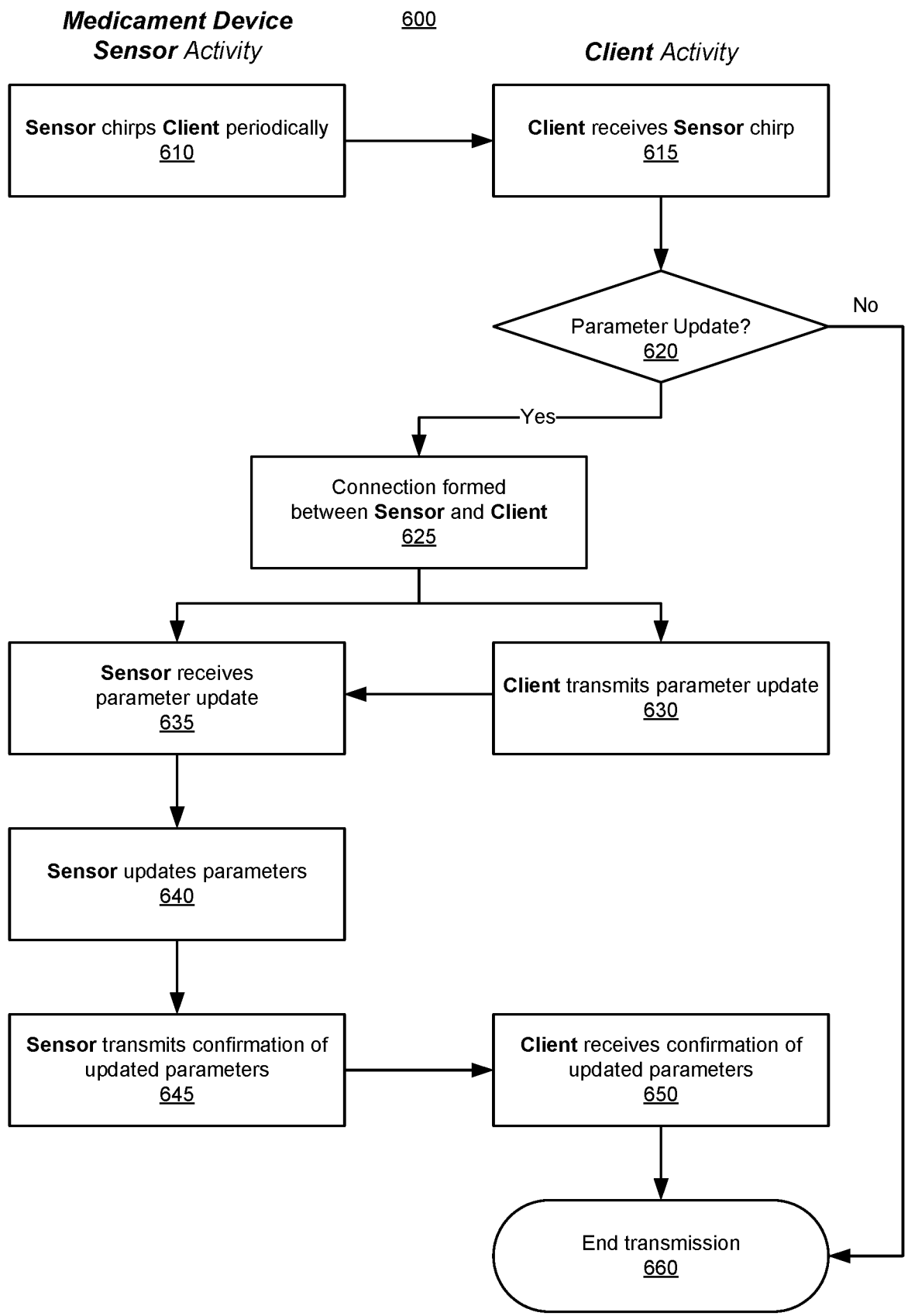
FIG. 6 is a flowchart describing updating parameters of a medicament device sensor through periodically chirping a client device prior to forming a wireless connection, according to one embodiment.

FIG. 6 is a flowchart describing updating parameters 600 of a medicament device sensor 120 through periodically chirping a client device 110 prior to forming a wireless connection, according to one embodiment. The medicament device sensor 120 (referred in the FIG. as "Sensor") as mentioned in FIGS. 4 & 5 may utilize Bluetooth Low Energy to chirp 610 the client device 110 (referred in the FIG. as "Client") periodically. The periodic chirp is similar to that described as chirping in FIGS. 4 & 5. As the client 110 receives the periodic chirping, the client 110 may respond to initiate a connection.

The client 110 determines 620 whether or not there is at least one set of parameter updates which are to be transmitted to the sensor 120. If so, the client 110 initiates 625 a Bluetooth connection with the sensor 120. After the sensor 120 and client 110 have been connected, in some instances using an authentication scheme, for Bluetooth Low Energy, the client 110 transmits 630 at least one set of parameter updates to the sensor 120. The sensor 120 receives 635 the set of parameter updates.

Upon receipt of the one or more sets of parameter updates, the sensor 120 updates 640 its parameters according to the one or more sets of parameter updates. Then the sensor 120 transmits 645 confirmation of updated parameters on the sensor 120. The client 110 receives 660 confirmation and may clear the sets of parameter updates. Finally, the client 110 ends 665 the Bluetooth connection, thus reverting the sensor 120 back to chirping, such as the Bluetooth Low Energy chirping mode 510 as described in conjunction with FIG. 5.

The client 110 can update a variety of parameters for the sensor 120. Examples include, but are not limited to: firmware updates and client-specific updates. The source of parameters for update may be related to the type of parameter. For example, firmware updates are typically received by the client 110 from a server providing the updates. The client 110 may prompt a user for some types of client-specific parameters to update. In some embodiments, the client 110 can be an application 115 on a mobile device displaying the dashboard 300 of FIG. 3 such that display cards 310 can prompt users for parameter updates. The user of the client 110 can input a response on the dashboard's input response 315. The updated parameters can then be logged in the client 110 prior to transmitting to the sensor 120. In one example, a user may set notifications for various tasks accomplished by the sensor 120 such as custom ringtones or medicament usage reminders.

Figure 7:
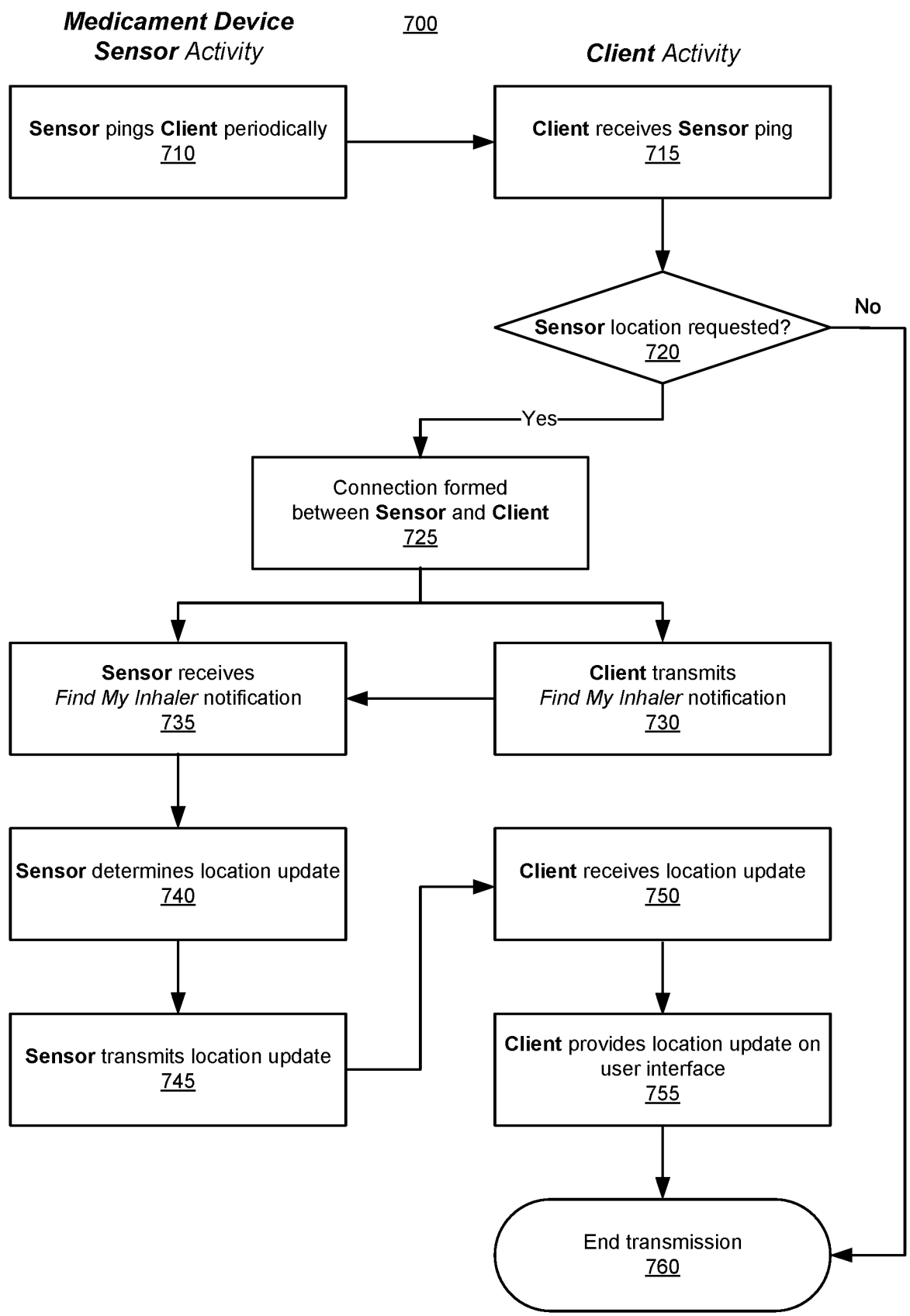
FIG. 7 is a flowchart describing locating a medicament device sensor through periodically pinging a client device prior to forming a wireless connection, according to one embodiment.

FIG. 7 is a flowchart describing a process for locating a medicament device sensor 120 by periodically chirping a client device 110 via wireless connection prior to forming a wireless connection, according to one embodiment. The medicament device sensor 120 (referred in the FIG. as "Sensor") as mentioned in FIGS. 4 & 5 utilizes Bluetooth Low Energy to chirp 710 the client device 110 (referred to in FIGS. 5-8 as simply the "Client") periodically. The periodic chirp is similar to that described as chirping in FIGS. 4 & 5. As the client 110 receives the periodic chirping, the client 110 may respond to initiate a connection. The client 110 determines 720 whether or not there is an initiated request for locating the sensor 120. In this illustration, the initiated request is part of "Find My Inhaler" protocol stored on the client 110; when initiated, the "Find My Inhaler" protocol executes the following steps between the client 110 and the sensor 120. If there is an initiated request for locating the sensor 120, the client 110 initiates 725 a Bluetooth connection with the sensor 120. After the sensor 120 and client 110 have been connected with each other, the client 110 transmits 730 a request for location information of the sensor 120. The sensor 120 receives 735 the request for location information of the sensor 120.

Upon receipt of the request for location information of the sensor 120, the sensor 120 determines 740 its location information. For example, the sensor 120 may include a GPS receiver such that when the sensor 120 receives a request for location information, the sensor 120 can record its GPS coordinates with a date and time. Upon receipt of the request for location information, the sensor 120 may additionally play an audio tune out of a loudspeaker device or similar audio playback unit on the sensor 120 to aid a user in physical proximity in locating the sensor 120. The sensor 120 transmits 745 the determined location information to the client 110. The client 110 receives 750 location information and provides 755 location information to the user, for example through the dashboard 300. The client 110 ends 760 the Bluetooth connection, thus reverting the sensor 120 back to chirping, such as the Bluetooth Low Energy chirping mode 510 as described in conjunction with FIG. 5.

Figure 8:
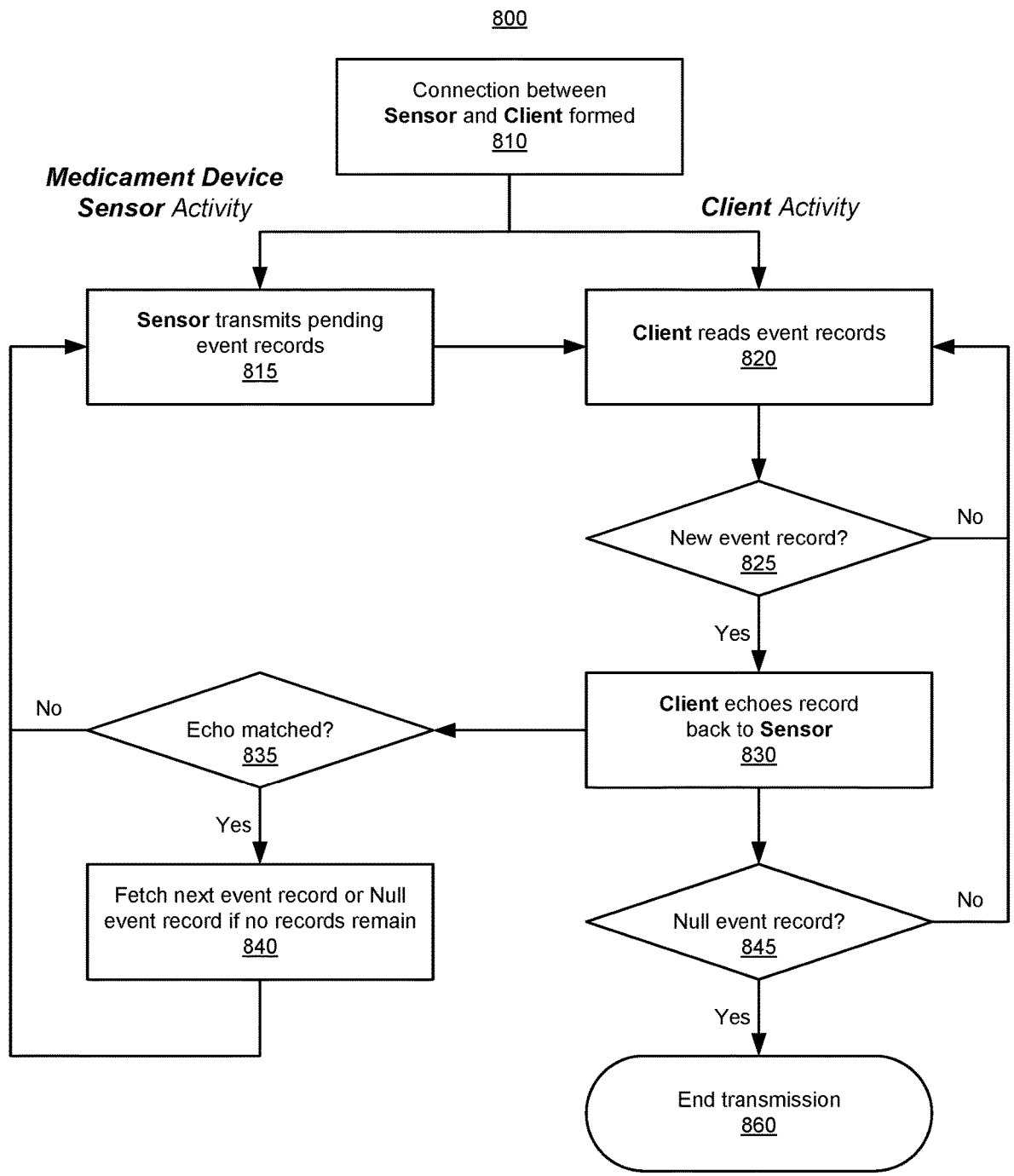
FIG. 8 is a flowchart describing transmitting recorded events from a medicament device sensor to a client device via a wireless connection, according to one embodiment.

FIG. 8 is a flowchart 800 for transmitting recorded events from a medicament device sensor 120 (sensor 120) to a client device 110 (client 110) via a wireless connection, according to one embodiment. The sensor 120 having recorded a medicament usage event, requests pairing with the client 110. The request for connecting with the client 110 may be chirped periodically with an adjusted chirping interval to be smaller. When the client 110 receives the chirp with the request for connection, the client 110 may form 810 a wireless connection. Upon forming 810 a wireless connection between the sensor 120 and the client 110, the sensor 120 transmits 815 pending event records to the client 110. The client 110 receives the 820 event records. The client 110 825 determines whether there are new event records or a null event record. If not, the client 110 waits for new event records from the sensor 120. If so, the client 110 echoes 830 event records back to sensor 120 and the client 110 845 determines whether event record is a null event record. Null event record represents no further pending event records to be transmitted. The sensor 120 receives echo and determines 835 whether echo matches transmitted event records. If not, the sensor 120 re-transmits 815 pending event records. If so, the sensor 120 fetches 840 next event record or null event record. The sensor 120 transmits 815 the fetched next event record or the fetched null record. When the client 110 determines 845 whether received event record is null, if so, the client 110 ends 860 transmission. If not, the client 110 waits for another event record. With the ended connection, the sensor 120 reverts back to chirping, such as the Bluetooth Low Energy chirping mode 510 as described in conjunction with FIG. 5.

VII. Additional Considerations

Although the discussion above focuses on asthma specifically, all systems and processes described herein are equally applicable to chronic obstructive pulmonary disease (COPD) and chronic respiratory disease (CRD) generally, and consequently can also be used to assist in treatment of COPD and CRD, as well as asthma.

It is to be understood that the figures and descriptions of the present disclosure have been simplified to illustrate elements that are relevant for a clear understanding of the present disclosure, while eliminating, for the purpose of clarity, many other elements found in a typical system. Those of ordinary skill in the art may recognize that other elements and/or steps are desirable and/or required in implementing the present disclosure. However, because such elements and steps are well known in the art, and because they do not facilitate a better understanding of the present disclosure, a discussion of such elements and steps is not provided herein. The disclosure herein is directed to all such variations and modifications to such elements and methods known to those skilled in the art.

Some portions of above description describe the embodiments in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

While particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

What is claimed is:

1. A computer-implemented method for transmitting events recorded by a medical inhaler sensor coupled to a medical inhaler to a client device, the method comprising:
   receiving, at the client device, a ping from the medical inhaler sensor;
   responsive to receiving the ping, forming, with the client device, a wireless connection between the medical inhaler sensor and the client device;
   receiving, from the medical inhaler sensor via the wireless connection, a first event record describing a first instance of medicament dispensing by the medical inhaler recorded by the medical inhaler sensor;
   transmitting, from the client device via the wireless connection, an echo of the first event record to the medical inhaler sensor;
   receiving, from the medical inhaler sensor via the wireless connection, a second event record at the client device;
   determining whether the second event record is a null event record, wherein a null event record confirms that the first event record is the most recent recording of medicament dispensing by the medical inhaler; and
   responsive to determining that the second event record is a null event record, terminating the wireless connection.

2. The method of claim 1, wherein the wireless connection is a Bluetooth Low Energy connection.

3. The method of claim 1, wherein the ping is received at the client device at a periodic interval.

4. The method of claim 3, wherein the periodic interval is adjusted between one or more of the following:
   an interval between 1 second and 60 seconds;
   an interval between 1 second and 15 seconds;
   an interval between 10 centiseconds and 100 centiseconds; and
   an interval between 10 milliseconds and 100 milliseconds.

5. The method of claim 1, wherein the ping is received at the client device in response to an event record indicating that a user actuated the medical inhaler to dispense medication to the user.

6. The method of claim 1, wherein event records comprise one or more of:
   a time of the instance of medicament dispensing;
   a battery life of the medical inhaler sensor;
   a type of recorded event; and
   a numeric identifier for the instance of medicament dispensing.

7. The method of claim 1, further comprising:
   comparing the echo of the first event record to the first event record transmitted by the medical inhaler sensor to determine if the echo matches the transmitted first event record; and
   responsive to determining that the echo of the first event record does not match the transmitted first event record, generating, by the client device, a second echo of the first event record; and
   transmitting, from the client device via the wireless connection, the second echo of the first event record to the medical inhaler sensor.

8. The method of claim 1, further comprising:
   responsive to determining that the second event record is not a null event record, transmitting, from the client device via the wireless connection, an echo of the second event record to the medical inhaler sensor;
   receiving, from the medical inhaler sensor, a third event record at the client device,
   determining whether the third event record is a null event record; and
   responsive to determining that the third event record is a null event record, terminating the wireless connection.

9. A non-transitory computer readable storage medium storing instructions for transmitting events recorded by a medical inhaler sensor coupled to a medical inhaler to a client device encoded thereon that, when executed by a processor, cause the processor to:
   receive a ping from the medical inhaler sensor;
   responsive to receiving the ping, form, with the client device, a wireless connection between the medical inhaler sensor and the client device;
   receive, from the medical inhaler sensor via the wireless connection, a first event record describing a first instance of medicament dispensing by the medical inhaler as recorded by the medical inhaler sensor;
   transmit, from the client device via the wireless connection, an echo of the first event record to the medical inhaler sensor;
   receive, from the medical inhaler sensor via the wireless connection, a second event record at the client device;

determine whether the second event record is a null event record, wherein a null event record confirms that the first event record is a most recent recording of medicament dispensing by the medical inhaler; and responsive to determining that the second event record is a null event record, terminate the wireless connection.

10. The non-transitory computer readable storage medium of claim 9, wherein the ping is received at the client device in response to an event record indicating that a user actuated the medical inhaler to dispense medication to the user.

11. The non-transitory computer readable storage medium of claim 9, wherein event records comprise one or more of:
a time of the instance of medicament dispensing;
a battery life of the medical inhaler sensor;
a type of recorded event, a temperature; and
a numeric identifier for the instance of medicament dispensing.

12. The non-transitory computer readable storage medium of claim 9, further comprising instructions that cause the processor to:
compare the echo of the first event record to the first event record transmitted by the medical inhaler sensor to determine if the echo matches the transmitted first event record; and
responsive to determining that the echo of the first event record does not match the transmitted first event record, generate, by the client device, a second echo of the first event record; and
transmit, from the client device via the wireless connection, the second echo of the first event record to the medical inhaler sensor.

13. The non-transitory computer readable storage medium of claim 9, further comprising:
responsive to determining that the second event record is not a null event record, transmitting, from the client device via the wireless connection, an echo of the second event record to the medical inhaler sensor;
receiving, from the medical inhaler sensor, a third event record at the client device,
determining whether the third event record is a null event record; and
responsive to determining that the third event record is a null event record, terminating the wireless connection.

14. A system comprising:
a medical inhaler sensor coupled to a medical inhaler, wherein the medical inhaler sensor records event records indicating when the medical inhaler is actuated to dispense medication to a user;
a non-transitory computer readable storage medium storing instruction for transmitting events recorded by the medical inhaler sensor to a client device encoded thereon that, when executed by a processor of the, cause the processor to:
receive, at the client device, a ping from the medical inhaler sensor;
responsive to receiving the ping, form, with the client device, a wireless connection between the medical inhaler sensor and the client device;
receive, from the medical inhaler sensor via the wireless connection, a first event record describing a first instance of medicament dispensing by the medical inhaler as recorded by the medical inhaler sensor, the first event record transmitted from the medical inhaler sensor to the client device;
transmit, from the client device via the wireless connection, an echo of the first event record to the medical inhaler sensor;
receive, from the medical inhaler sensor via the wireless connection, a second event record at the client device, the second event record transmitted from the medical inhaler sensor to the client device;
determine whether the second event record is a null event record, wherein a null event record confirms that the first event record is a most recent recording of medicament dispensing by the medical inhaler; and
responsive to determining that the second event record is a null event record, terminate the wireless connection.

15. The system of claim 14, wherein event records comprise one or more of:
a time of the instance of medicament dispensing;
a battery life of the medical inhaler sensor;
a type of recorded event, a temperature; and
a numeric identifier for the instance of medicament dispensing.

16. The system of claim 14, further comprising instructions that cause the processor to:
compare the echo of the first event record to the first event record transmitted by the medical inhaler sensor to determine if the echo matches the transmitted first event record; and
responsive to determining that the echo of the first event record does not match the transmitted first event record, generate, by the client device, a second echo of the first event record; and
transmit, from the client device via the wireless connection, the second echo of the first event record to the medical inhaler sensor.

17. The system of claim 14, further comprising:
responsive to determining that the second event record is not a null event record, transmitting, from the client device via the wireless connection, an echo of the second event record to the medical inhaler sensor;
receiving, from the medical inhaler sensor, a third event record at the client device,
determining whether the third event record is a null event record; and
responsive to determining that the third event record is a null event record, terminating the wireless connection.

* * * * *

UNITED STATES PATENT AND TRADEMARK OFFICE
CERTIFICATE OF CORRECTION

| | | |
|---|---|---|
| PATENT NO. | : 11,462,323 B2 | Page 1 of 1 |
| APPLICATION NO. | : 17/043586 | |
| DATED | : October 4, 2022 | |
| INVENTOR(S) | : Samuel A. Koblenski et al. | |

It is certified that error appears in the above-identified patent and that said Letters Patent is hereby corrected as shown below:

In the Claims

In Claim 14, at Column 21, Line 49: Please delete "instruction" and add --instructions-- after "a non-transitory computer readable storage medium storing..."

In Claim 14, at Column 21, Line 52: Please delete "of the" before "..., cause the processor to:..."

Signed and Sealed this
Thirtieth Day of July, 2024

Katherine Kelly Vidal
*Director of the United States Patent and Trademark Office*